United States Patent [19]

Nelsen et al.

[11] Patent Number: 4,753,799
[45] Date of Patent: Jun. 28, 1988

[54] PRODUCTION OF HYDROGEL ENCAPSULATED NEMATODES

[75] Inventors: Charles E. Nelsen, Davis, Calif.; Catharine Mannion, Raleigh, N.C.

[73] Assignee: Plant Genetics, Inc., Davis, Calif.

[21] Appl. No.: 96,897

[22] Filed: Sep. 14, 1987

Related U.S. Application Data

[62] Division of Ser. No. 864,832, May 19, 1986, Pat. No. 4,701,326, and Ser. No. 790,337, Oct. 23, 1985, Pat. No. 4,615,883.

[51] Int. Cl.[4] ............................................. A01N 63/00
[52] U.S. Cl. ...................................... 424/408; 119/1; 119/15; 43/55; 426/1; 424/93
[58] Field of Search ..................... 119/1, 15; 424/408, 424/93; 43/55; 426/1

[56] References Cited

U.S. PATENT DOCUMENTS

| | | | |
|---|---|---|---|
| 2,735,215 | 2/1956 | Rutledge | 43/55 |
| 2,809,463 | 10/1957 | Buss | 43/55 |
| 2,841,113 | 7/1958 | Ebert | 43/55 |
| 2,961,319 | 11/1960 | Stephan | 426/1 |
| 3,115,864 | 12/1963 | Wagner | 43/55 |
| 3,361,566 | 1/1968 | Axelrod | 426/1 |
| 3,541,203 | 11/1970 | Fogle | 424/84 |
| 3,545,404 | 12/1970 | Loftus | 426/1 |
| 3,767,790 | 10/1973 | Guttag | 424/81 |
| 3,931,414 | 1/1976 | Popeil | 426/1 |
| 4,178,366 | 12/1979 | Bedding | 424/93 |
| 4,202,905 | 5/1980 | Asai et al. | 426/1 |
| 4,298,002 | 11/1981 | Ronel et al. | 424/19 |
| 4,352,883 | 10/1982 | Lim | 424/35 |
| 4,391,909 | 7/1983 | Lim | 424/35 |
| 4,409,331 | 10/1983 | Lim | 424/93 |
| 4,486,460 | 12/1984 | Kienast et al. | 426/1 |
| 4,487,759 | 12/1984 | Nesbitt | 424/84 |
| 4,503,077 | 3/1985 | Horton | 426/1 |
| 4,551,333 | 11/1985 | Neri | 426/1 |
| 4,615,883 | 10/1986 | Nelsen et al. | 424/408 |
| 4,701,326 | 10/1987 | Nelsen et al. | 424/408 |

FOREIGN PATENT DOCUMENTS

| | | | |
|---|---|---|---|
| 0097571 | 1/1984 | Euroepan Pat. Off. | 424/93 |
| 0180588 | 9/1985 | Japan | 424/93 |
| WO84/01287 | 4/1984 | PCT Int'l Appl. | 424/93 |

*Primary Examiner*—Shep K. Rose
*Attorney, Agent, or Firm*—Limbach, Limbach & Sutton

[57] ABSTRACT

Method and composition for an insecticide comprising a hydrated hydrogel capsule containing an insecticidally effective amount of at least one nematode capable of infecting an insect host, which capsule has sufficient hydration to maintain the viability and infectivity of said nematode. Also disclosed are methods for providing said insecticidal compositions.

6 Claims, No Drawings

PRODUCTION OF HYDROGEL ENCAPSULATED NEMATODES

RELATED APPLICATION DATA

This application is a divisional application of Ser. No. 864,832, filed May 19, 1986, now U.S. Pat. No. 4,701,326, and a divisional application of Ser. No. 790,337, filed Oct. 23, 1985, now U.S. Pat. No. 4,615,883.

DESCRIPTION

TECHNICAL FIELD

The present invention relates generally to the use of nematodes as insecticides, and more particularly to immobilizing and preserving nematodes in hydrogel capsules for delivery to insect hosts, and to hydrogel capsules containing nematodes.

BACKGROUND ART

There has been increasing interest in the use of living organisms to control the spread of detrimental insects through agricultural areas. Such insecticidal agents are desirable in order to avoid the drawbacks associated with chemical insecticides, such as their lack of specificity, residual toxic effects and the rapid development of resistance by the targeted insects. Living insecticide agents, when delivered under controlled conditions, have narrow host ranges and can control the spread of specific hosts, without affecting natural predators or beneficial insects. Examples of such agents, termed bio-rational insecticides, include *Bacillus thuringiensis*; Baculoviridae, such as *Autographa californica* nuclear polyhedrosis virus; and various fungal pathogens, among others.

Nematodes have long been considered a desirable insecticide agent due, in part, to their wide variety of target or host organisms. For example, steinernematids and heterorhabditid nematodes display a broad host range under laboratory conditions which exclude behaviorial or ecological barriers to nematode infection, Poinar, G. O., *Nematodes for Biological Control of Insects*, CRC Press, Inc., Boca Ratan, Fla. (1979); Gaugler, R., J. Nematol. 13:241–249 (1981). The insecticidal effect generally results from the nematodes own pathogenicity towards insects, as well as its association with certain entomogenous bacteria. For example, the infective larvae of *Neoaolectana carpocapsae* have an associated bacteria *Achromobacter nematoohilus*, usually found in the intestinal lumen. Following ingestion by an insect, or invasion of the insect, the nematode will usually penetrate the gut wall and enter the hemocoel, whereupon the bacteria will be released and multiply to produce fatal septicaemia in the host.

A major obstacle to the use of nematodes as insecticides has been their susceptibility to desiccation. In the field, the effective host range is limited, by the nematodes moisture requirement, to insects inhabiting the soil and cryptic habitats including, e.g., greenhouses, mushroom beds and animal dung. There have been numerous attempts to increase field persistance and utilize nematodes for control of insects in the open by avoiding diurnal application or employing anti-desiccants or humectants.

This moisture requirement has led to various aqueous formations containing nematodes, whose effectiveness is generally limited by premature evaporation of the aqueous carrier. In order to reduce the rate of evaporation, aqueous carriers have included evaporation-retardant water thickeners, mineral oil, gelling agents or surfactants. See, for example, U.S. Pat. No. 4,178,366.

Hydrogel agents have been employed for the encapsulation of numerous microorganisms or cell cultures as well as organic and bio-active chemicals. Representative of such encapsulations are U.S. Pat. Nos. 4,450,233; 4,352,883; 4,434,231.

It would be desirable to encapsulate multi-cellular organisms, such as nematodes, in a matrix which supplies sufficient moisture to prevent desiccation, yet allows the infective stage of the nematode to be ingested by or invade a broad range of insect hosts.

DISCLOSURE OF THE INVENTION

An important object of the present invention is to provide an insecticidal composition which can be delivered to field locations with sufficient moisture to provide insecticidally effective amounts of nematodes enclosed therein for extended periods of time.

The present invention attains this and other objects by providing methods and materials for the encapsulation of infective nematodes in hydrated hydrogel capsules, which capsules sustain the nematodes' viability and infectivity for a substantial period of time without impairing their infection of insect hosts.

In accordance with one aspect of the present invention, an insecticidal composition is provided comprising a hydrated hydrogel capsule containing an insecticidally effective amount of at least one nematode capable of infecting an insect host, which capsule has sufficient hydration to maintain the viability and infectivity of said nematode.

A further aspect of the present invention comprises such an insecticidal composition together with at least one agent capable of attracting prospective insect hosts.

A still further aspect of the present invention comprises an insecticidal composition of a hydrated hydrogel capsule containing an insecticidally effective amount of at least one nematode capable of infecting an insect host, together with at least one agent capable of stimulating the ingestion of said capsule by said insect host. Also provided are methods for producing such insecticidal compositions.

BEST MODE OF PRACTICING THE INVENTION

Numerous pathogenic nematodes have been recognized in the prior art as having a broad range of host insects, and therefore provide desirable insecticidal agents for the practice of the present invention.

Perhaps the best known nematode useful as an insecticidal agent is the infective stage larvae of *Neoaplectana carpocapsae* Weiser (*Steinernema feltiae* Filipjev). Other nematodes known to be capable of producing insecticidal effects include:

Family Steinernematidae
  *Neoaplectana glaseri*
  *Neoaplectana menozzii* (=*Steinernema kraussei*)
  *Neoaplectana bibionis*
  *Neoaplectana kirjanovae* (=*Steinernema glaseri*)
  *Neoaplectana georgica* (=*Steinernema bibionis*)
  *Neoaplectana dutkyi*
Family Heterorhabditidae
  *Heterorhabditis bacteriophora*
  *Heterorhabditis heliothidis*
  *Heterorhabditis hoptha*

*Heterorhabditis hambletoni*
Family Mermithidae
 *Filipjevimermis leipsandra*
 *Reesimermis nielseni* (=*Romanomermis culicivorax*)
 *Diximermis petersoni*
 *Hexamermis arvalis*
 *Mermis nigrescens*
 *Pheromermis pachysoma*
Other families which contain species that can cause insect death:
 Carabonematidae
 Diplogasteridae
 Rhabditidae
 Sphaerulariidae
 Tetradonematidae In addition there are many entomogenous nematodes that cause insect sterility and the attendant decline in the insect host population.

Many of the nematodes disclosed above are capable of being reared under controlled conditions. One method is by infecting selected insect hosts and suspending the resultant insect carcass in an aqueous environment. The nematodes can then be collected from the water over a substantial period of time. See Poinar, supra.

Alternatively, nematodes can be reared in a growth chamber such as disclosed in U.S. Pat. No. 4,334,498, the relevant portions of which are incorporated herein by this reference.

Various hydrogel agents can be employed to provide an appropriate encapsulation matrix for the insecticidal compositions produced in accordance with the present invention. In general, a hydrogel capsule should allow nematode respiration by permitting diffusion of gases. The hydrogel agent selected should provide a capsule strong enough to resist external abrasion and adverse forces, yet be pliable enough to allow the eventual release of the nematode or ingestion by the insect at the appropriate time. In order to fulfill these objectives, it may be desirable in certain embodiments to use various gels in combination, either as a mixture or in layers, to achieve the desired results.

Hydrogel agents useful for providing hydrated hydrogel capsules for encapsulating nematodes include sodium alginate, guar gum, carrageenan with locust bean gum, and sodium alginate with gelatin. Other suitable hydrogel agents include, but are not limited to:

TABLE 1

| HYDROGEL AGENTS |
| --- |
| I. Natural Polymers |
|   A. Ionic bonds |
|     (requires complexing agents) |
|     Alginate with Polypectate Sodium Pectate |
|     Furcellaran |
|     Pectin |
|     Hypnean |
|     Dextran |
|     Tamarind |
|     Guar Gum |
|     Gellan Gum |
|   B. Hydrophobic Interactions Amylose |
|     Agar |
|     Agarose |
|     Agar with Gelatin |
|     Gelatin |
|     Starch |
|     Amylopectin |
|     Cornhull Gum |
|     Starch Arabogalactan |
|     Gum Ghatti |
|     Gum Karagan |
|     Ti Gum |
|     Gum Tragacanth |
|     Wheat Gum |
|     Chitin |
|     Dextrin |
| II. Stabilizing Compounds |
|   A. Trade Names |
|     Gelrite ® (Kelco) |

Other hydrogel agents which provide similar characteristics will be employed as equivalents to those disclosed above.

A hydrogel agent chosen for encapsulation of nematodes would usually include the following characteristics (although the invention may be practiced in other modes):

1. A hydrogel capsule compliance adequate to protect and cushion the nematodes;

2. The interior of the hydrogel capsule would have solubility or emulsion-forming characteristics such that it can accept and contain additives, including but not limited to aqueous, non-soluble, or hydrophobic substances which are capable of attracting the insect to the capsule or, stimulating ingestion of the capsule by the insect;

3. An outer surface which provides a protective barrier to mechanical stress, facilitates handling, and maintains capsule hydration and concommitant nematode viability and infectivity;

4. Sufficient mechanical gel strength to maintain capsule integrity, while allowing the nematodes to migrate out to the insect host, and allowing any contained attractant additives to be released.

5. The selected agent should form a capsule matrix at temperatures and under conditions which the nematodes find tolerable, and should not require the use or production of any component detrimental to nematode longevity or infectivity. It will be understood however that nematodes will be able to temporarily withstand such conditions without permanent impairment.

The hydrogel capsule characteristics described above are determined generally by the concentration parameters and chemical properties of the hydrogel agent employed and it will be readily appreciated that these features can range widely in particular applications without departing from the scope of the invention.

A presently preferred embodiment of the invention employs a sodium alginate hydrogel agent such as LF-60 (supplied by Multi-Kem, Ridgefield, N.J.). This hydrogel agent can be dissolved in water in varying concentrations to form an alginate solution and nematodes can be added to the resultant solution in concentrations sufficient to provide insecticidally effective amount of nematodes in each resultant capsule.

This alginate solution, for example, will form a hydrogel capsule when the hydrogel agent is added to a complexing agent. Calcium chloride ($CaCl_2$) is generally used, however, lanthanum chloride, ferric chloride, cobaltous chloride, calcium nitrate and calcium hydroxide are also acceptable, as generally are other compounds with multivalent cations, such as calcium ($Ca^{++}$), copper ($Cu^{++}$) and the like.

A chosen hydrogel agent will have a range of concentrations usable in working the invention. A concentration will ordinarily be chosen to optimize ease of handling, gelling time, the strength of the hydrogel capsule and the desired coating thickness around the nematodes. For example, the sodium alginate solution can be prepared in a concentration of 1 to 10% w(in grams)/v(in milliliters) in water, more usually 1.5 to 5% and desirably from approximately 1.5 to 3%. However, if the hydrogel agent concentration is too great, the solution may be so viscous as to hinder immersion and mixing of the nematodes in the hydrogel solution, or result in damage to the nematodes due to viscosity sheer effects.

Hydrogel capsules can be formed from the sodium alginate solution containing nematodes, for example, by adding the solution drop-wise to the selected complexing agent. Alternatively, the hydrogel solution and complexing agent may be mixed by any of numerous techniques known to the art. These may include droplet formation and agent addition as a one step process by a vibrating nozzle which ejects a hydrogel droplet from one source and coats the droplet with complexing agent from another.

The calcium chloride (or other complexing agent) may be made up in solution at a concentration of 1 to 1,000 millimolar, more usually 20 to 500 millimolar and desirably from 50 to 100 millimolar. Other complexing agents will have different preferred concentration ranges. The droplets of alginate containing the nematodes can then be treated with the calcium chloride (or other complexing agent) solution by soaking, spraying, dipping, pouring or any of several other methods which will deposit an amount of the complexing agent on the droplet. When soaking such droplets in $CaCl_2$ solution, the time in solution may be from 1 second to 24 hours, more usually 1 minute to 1 hour, and ideally from 10 to 30 minutes.

The time for hydrogel formation and the temperature of the gelling solutions are understood to be interrelated parameters, for selected concentrations of hydrogel agent and complexing agent. The temperature should be chosen so as to avoid damage to the nematodes, usually in the range of 1° to 50° C., more usually 10° to 40° C., and preferably at 15° to 30° C.

Within the range of acceptable temperatures, a particular value may be chosen to give the shortest possible gelling time consistent with complete hydrogel formation. Typically, the hydrogel matrix will form immediately, but the full complexation takes longer. For a solution of sodium alginate at a concentration of 2.0 grams per 100 milliliters $H_2O$, calcium chloride solution concentration of 100 millimolar and 25° C. reaction temperature, adequate gelling is obtained in 5 to 120 minutes, more often 10 to 90 minutes and is usually sufficiently complete in 15 to 30 minutes.

This hydrogel encapsulation procedure is designed to maintain a high level of free water within the capsule. The external surface of the capsule is formed by a chemical reaction between the gel and complexing agent. The interior of the capsule remains wet, having a water content in excess of fifty percent, preferably between seventy and ninety-eight percent. This water is immediately available to the nematodes within the capsule, thereby providing the anti-desiccation moisture requirement which constitutes an important element in maintaining nematode viability and infectivity. The water content of the hydrated capsule can be adjusted after formation by partial desiccation, e.g., with an appropriate osmoticum such as polyethylene glycol.

Hydrated hydrogel capsules containing insecticidally effective amounts of nematodes prepared in accordance with the present invention will range in size from approximately 0.4 to 5 millimeters in diameter and contain approximately 250–50,000 nematodes per milliliter. The amount of nematodes per unit volume necessary to be insecticidally effective will vary in accordance with the nematode selected and the particular insect host. This amount can be determined routinely once a particular application has been selected. It is also understood that the nematode concentration need not be uniform throughout the capsule. Certain embodiments may provide discontinuous distributions of nematodes, such as greater concentrations in the core of the capsule, while preserving the benefits of the present invention.

A further aspect of the present invention is the encapsulation of nematodes in hydrated hydrogel capsules together with agents capable of attracting desired insect hosts. Such agents, also termed baits can include, for example, foods such as commercial formulations for the rearing of insects, chemical attractants, pheromones, and the like.

It is also considered desirable in some situations that the attractant agent stimulate the insect to ingest the capsule, thereby increasing the insecticidal effect of the composition by reducing the need for the nematodes to migrate from the capsule. Alternatively, a distinct agent can be provided separately or in combination with the attractant agent which stimulates the ingestion of the capsule by the prospective insect host. Examples of agents found useful for attracting insects or stimulating ingestion are as follows:

TABLE 2

| BAITS |
| --- |
| Bran |
| Wheat germ |
| Sucrose |
| Fungal decayed sawdust. |
| Insect pheromones |
| Plant/root material or exudates |
| Shorey and Hale's insect diet |
| Other insect diets and feeding stimulants |

Having described the present invention in detail, the following examples of particular embodiments of the present invention, provided for purposes of illustration, should not be construed as implying a limitation on the scope of the appended claims.

Experimental

In order to demonstrate the invention, the following examples are provided to portray a variety of nematodes, hydrogel agents and attractants and ingestion stimulants. All quantities labeled percent are grams per 100 milliliters, unless otherwise indicated.

EXAMPLE I

*Neoaplectana carpocapsae* Weiser nematodes were produced in *Galleria mellonella* L. larvae as described in Dutky, et al., J. Insect Pathol 6:417–422 (1964). After approximately four days, the insect host carcass are placed in collecting dishes with water and nematodes are harvested for approximately one week. Harvested nematodes were stored in 250 $cm^3$ tissue culture flasks at approximately 34,000 nematodes per milliliter at 4° C.

2 grams of LF-60 sodium alginate (Multi-Kem, Ridgefield, N.J.) was dissolved in 100 ml of water in a commercial blender by stirring for approximately four to five minutes. Infective stage larvae of the nematodes were mixed in the sodium alginate solution so as to provide approximately 4,000 nematodes per milliliter. The solution containing the nematodes was then ladded drop-wise into a complexing agent containing 100 mM $CaCl_2$ $2H_2O$. This complexing agent solution was subject to continuous stirring during the addition of the alginate solution to avoid localized exhaustion of the divalent cation.

After approximately 20 to 30 minutes complexation time, capsules were separated from the complexing solution by sieving and were rinsed in deionized water. These capsules were then stored in a humid environment at approximately 4° C.

After storage for periods up to 9 months, the viability and infectivity of the encapsulated nematodes were determined as follows:

Samples of each capsule were dissolved by immersion in 0.5M sodium citrate as a dissolving agent. The solution containing the nematodes was diluted in water and the viable nematodes were counted under a dissecting microscope.

An insect host is then placed in a 50 ml beaker, covered with sand containing approximately 7% water and inoculated with the nematode. The beaker is covered to retard desiccation and insect mortality is scored after seven days.

The results of these assays are displayed in Table 3.

TABLE 3

BIOASSAY RESULTS

| Treatment | % Larval Mortality |
|---|---|
| Example I. A | |
| 1. Nematodes stored 9 months in solution | 100 |
| 2. Nematodes stored 9 months in large (@ 90 mg) capsules | 70 |
| 3. Nematodes stored 9 months in small (169 30 mg) capsules | 90 |
| 4. No nematodes | 10 |
| Example I. B | |
| 1. Nematodes stored 5 months in solution | 100 |
| 2. Nematodes stored 5 months in capsules complexed with $CaCl_2$ | 90 |
| 3. Nematodes stored 5 months in capsules complexed with $CuSO_4$ | 100 |
| 4. No nematodes | 0 |
| Example I. C | |
| 1. Nematodes stored 2 months in solution | 100 |
| 2. Nematodes stored 2 months in capsules (@ 200/cap.) | 100 |
| 3. Nematodes stored 2 months in capsules (@ 1000/cap.) | 100 |
| 4. Nematodes stored 2 months in capsules (@ 2000/cap.) | 100 |
| 5. Nematodes stored 2 months in capsules (@ 3000/cap.) | 100 |
| 6. Nematodes stored 2 months in capsules (@ 4000/cap.) | 80 |
| 7. No nematodes | 0 |

EXAMPLE II

The encapsulation procedure described in Example I was repeated employing the nematode *Heterorhabditis heliothidis* in place of *Neoaplectana carpocapsae*, with similar results for shorter storage periods.

EXAMPLE III

*Neoaplectana carpocapsae* nematodes were encapsulated in accordance with the procedure described in Example 1, with the following modification:

Shorey and Hale's insect diet[1] was dissolved in the sodium alginate solution at a concentration of approximately 1 ml diet/4 ml gel solution and encapsulated together with the nematodes.

[1] H. H. Shorey and R. L. Hale, Mass-Rearing of the Larve of Nine Noctuid Species on a Simple Artificial Medium, Journal of Economic Entomology, 1965, 58: 522–524.

Capsules thus prepared were presented to the following insect hosts: *Spodoptera exigua, Pseudaletia unipuncta*, without additional food or water for 24 to 48 hours. Thereafter the capsules were removed and alternative sources of normal food and water were presented. Subsequent insect mortality was determined for a period of three days. The results were as indicated in Table 4.

TABLE 4

| Nematode Delivery | Percent Larval Mortality | | | | |
|---|---|---|---|---|---|
| TREATMENT Nematodes Delivered In: | Time 0 | 1 Hour | 2 Hours | 3 Hours | 4 Hours |
| EXAMPLE III. A | | | | | |
| Water | 100 | 20 | 20 | 0 | 40 |
| Capsule | 100 | 80 | 40 | 40 | 80 |
| Capsule + Membrane | 60 | 60 | 100 | 100 | 60 |
| EXAMPLE III. B | | | | | |
| Water | 100 | 100 | 0 | 0 | 20 |
| Capsule | 100 | 80 | 40 | 20 | 0 |
| Capsule + Membrane | 80 | 100 | 100 | 100 | 60 |
| EXAMPLE III. C | | | | | |
| Water | 100 | 80 | 20 | 0 | 0 |
| Capsule | 80 | 80 | 40 | 0 | 0 |
| Capsule + Membrane | 20 | 100 | 80 | 80 | 60 |
| MEAN OF EXPERIMENTS | | | | | |
| Water | 100.0 | 66.7 | 13.3 | 0 | 20.0 |
| Capsule | 93.3 | 80.0 | 40.0 | 20.0 | 26.7 |
| Capsule + Membrane | 53.3 | 86.6 | 93.3 | 93.3 | 60.0 |

EXAMPLE IV

Nematodes were encapsulated in hydrogel capsules as described in Example I, and in addition, the capsules were coated with an outer membrane to reduce water loss from the capsule. This capsule membrane was prepared in accordance with the following protocol:

CAPSULE MEMBRANE PROTOCOL

I. Solution Preparation

A. Pretreatment Solution

Stir calcium oxide in millipore filtered water (1:100, w:v) for 15 minutes. Filter resulting suspension through Whatman #1 with funnel and save filtrate. Keep filtrate tightly sealed.

B. Membrane Solutions

1. Elvax solution

Prepare a solution of Elvax 4260 (Dupont, Wilmington, Del.) in Cyclohexane (1:10, w/v). The density$^{-1}$ of Cyclohexane is 1.32 mls/gm, therefore, a solution of 1 gm of Elvax in 10 gm of Cyclohexane equals 1 g of Elvax in 13.2 ml of Cyclohexane. Add the Elvax to the Cyclohexane while the latter is stirring. As the solution thickens, increase the rate of stirring and heat gently using the "LO" setting on a Corning Hot Plate Stirrer (PC-351). Keep the solution covered with foil.

2.

Prepare the "wax" additives Weigh out a 5:2:1 (w,w,w) preparation of Spermaceti wax substitute #573 (F. B. Ross, Jersey City, N.J.), Cetyl Alcohol (1-hexandecanol), and Stearic Acid. Combine all three in a large beaker (600–1,000 ml) cover, and heat on "LO" on hot plate for 10–20 minutes or until melted.

3.

Combine membrane ingredients a. obtain Petroleum Ether (50°–100° C.) and Methylene Chloride (Dichloromethane)

b. ratio by weight of combined ingredients is:
IB1.

10 Elvax in Cyclohexane

5 Spermaceti wax subs.

IB2.

2 cetyl Alcohol

1 Stearic Acid

IB3.

40 Pet Ether ($Density^{-1}=1.48$ ml/gm)

40 Methylene Dichloride ($Density^{-1}=0.78$ ml/gm)

Pour IB1. into IB2. with gentle stirring. Add IB3. to other 2 with continued stirring. Store in sealed container in dark.

II. Membrane Application

A.

Pretreat capsules with solution IA. (calcium oxide filtrate) for 1 minute with swirling or stirring; 2:1 (v/v) capsules: pretreatment solution. Decant the pretreatment solution through Nylon mesh and remove excess solution with a towel. Dip capsules, held in nylon mesh, in excess membrane solution IB3. for 15 seconds, allow to drain briefly over solution. Blow dry capsules with hand-held hair dryer on low temperature (2 to 3 minutes). Repeated dipping and drying will increase thickness of membrane deposition. Allow capsules to air dry for 3 to 4 hours to further evaporate solvents and seal pinholes.

The capsules thus prepared were presented to the following insect hosts: *Spodoptera exigua, Pseudaletia unipuncta*, without additional food or water for 24 to 48 hours. Thereafter the capsules were removed and alternative sources of normal food and water were presented. Subsequent insect mortality was determined for a period of three days. The results were as indicated in Table 4.

It is seen that substantial improvements in the insecticidal capability of nematodes are obtained by providing insecticidal compositions in accordance with the present invention. The hydrogel encapsulation of insecticidally effective amounts of nematodes resulted in generally increased insect host mortality compared to nematodes submersed in water. Furthermore, such encapsulated nematodes, when provided with a capsule membrane in accordance with the invention, demonstrate dramatic improvements in retained insecticidal activity over an extended period of time. In this manner, the present invention attains the objects described above, among others.

Although the foregoing invention as been described in some detail by way of illustration for purposes of clarity of understanding, it will be readily appreciated that numerous modifications may be practiced within the spirit and scope of the appended claims.

We claim:

1. A method for producing an insecticidal composition comprising the steps of:

providing a mixture comprising at least one hydrogel agent capable of forming a hydrated hydrogel capsule and an insecticidally effective amount of at least one nematode having an associated entomogenous bacteria, usually found in the intestinal lumen, which, following ingestion of the nematode by an insect host, said entomogenous bacteria will be released and multiply to produce fatal septicaemia in the insect host; and forming, without excess viscosity-caused damage, a hydrated hydrogel capsule from said mixture which capsule allows nematode respiration by permitting diffusion of gases and has sufficient hydration to maintain the viability and infectivity of said nematode, said capsule being strong enough to resist external abrasion yet being pliable enough to allow the eventual release of the nematode or injection by the insect, said capsule ranging in size from approximately 0.4 to 5 millimeters in diameter and containing approximately 250 to 50,000 nematodes per milliliter, and the interior of said capsule remaining wet and having a free water content in excess of 50 percent, said free water being immediately available to the nematodes in the capsule, thereby providing the anti-dessication moisture element for maintaining nematode viability and infectivity.

2. A method as recited in claim 1 wherein said gel agent is at least one member selected from the group consisting of sodium alginate, gelatin, guar gum, and carrageenan.

3. A method as recited in claim 1 wherein said nematode is at least one member selected from the group consisting of *Neoaplectana carpocapsae* and *Heterorhabditis heliothidis.*

4. A method as recited in claim 1 further comprising including in said mixture at least one agent capable of attracting said insect host to said capsule.

5. A method as recited in claim 1 further comprising including in said mixture at least one agent capable of stimulating the ingestion of said capsule by said insect host.

6. A method as recited in claim 1 further comprising substantially coating said capsule with at least one membrane which is capable of reducing the rate of water loss from said capsule while allowing nematode respiration by permitting diffusion of gases.

* * * * *